United States Patent [19]

Takaya et al.

[11] 4,220,761
[45] Sep. 2, 1980

[54] 7-[SUBSTITUTED OXIMINOACETAMIDO]-3-[HYDROXY ALKYLTETRAZOLO]CEPHALOSPORIN DERIVATIVES

[75] Inventors: Takao Takaya, Kawanishi; Takashi Masugi, Kitamachi; Hisashi Takasugi, Kohamanishi; Hiromu Kochi, Sakai, all of Japan

[73] Assignee: Fujisawa Pharmaceutical Co., Ltd., Osaka, Japan

[21] Appl. No.: 941,660

[22] Filed: Sep. 12, 1978

[51] Int. Cl.² .............................................. C07D 501/36
[52] U.S. Cl. ........................................ 544/27; 424/246
[58] Field of Search ...................... 544/27, 28; 424/246

[56] References Cited

U.S. PATENT DOCUMENTS

| 4,080,498 | 3/1978 | Numata et al. | 424/246 |
| 4,098,888 | 7/1978 | Ochiai et al. | 424/246 |

Primary Examiner—Glennon H. Hollrah
Assistant Examiner—David E. Wheeler
Attorney, Agent, or Firm—Dayton R. Stemple, Jr.

[57] ABSTRACT

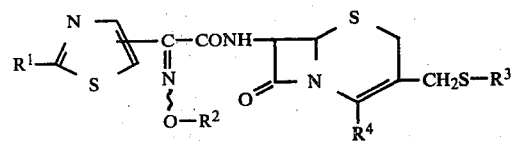

wherein
$R^1$ is amino or protected amino,
$R^2$ is an aliphatic hydrocarbon residue which may be substituted with hydroxy, protected hydroxy or lower alkylthio,
$R^3$ is a heterocyclic group substituted with amino(lower)alkyl, protected amino(lower)alkyl or hydroxy(lower)alkyl, and
$R^4$ is carboxy or functionally modified carboxy, "syn" or "anti" isomer.

8 Claims, No Drawings

7-[SUBSTITUTED OXIMINOACETAMIDO]-3-[HYDROXY ALKYLTETRAZOLO]CEPHALOSPORIN DERIVATIVES

This invention relates to new cephem compound. More particularly, it relates to new 7-substituted-3-cephem-4-carboxylic acid, its pharmaceutically acceptable salt and pharmaceutically acceptable bioprecursor thereof, which have antimicrobial activities, and processes for preparation thereof, to pharmaceutical composition comprising the same and methods of using the same prophylactically and therapeutically for treatment of infectious diseases in human being and animals.

Accordingly, the objects of this invention are to provide:

new 7-substituted-3-cephem-4-carboxylic acid, its pharmaceutically acceptable salt and pharmaceutically acceptable bioprecursor thereof, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals.

The cephem compound provided by this invention can be represented by the formula (I):

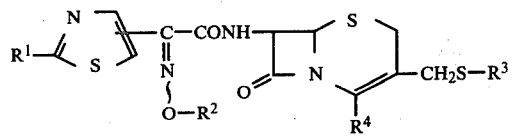

wherein
$R^1$ is amino or protected amino,
$R^2$ is an aliphatic hydrocarbon residue which may be substituted with hydroxy, protected hydroxy or lower alkylthio,
$R^3$ is a heterocyclic group substituted with amino(lower)alkyl, protected amino(lower)alkyl or hydroxy(lower)alkyl, and
$R^4$ is carboxy or functionally modified carboxy.

The terms and definitions described in this specification are illustrated as follows.

(a) Partial structure of the formula:

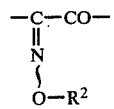

is intended to mean both of the geometric formulae:

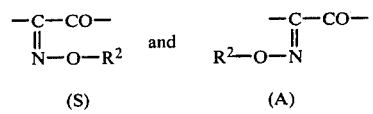

The geometry of the formula (S) is referred to as "syn" and another formula (A) is referred to as "anti".

Accordingly, one isomer of the above formula (S) is referred to as "syn isomer" and another isomer of the above formula (A) is referred to as "anti isomer", respectively.

From the view point of structure-activity relationship, it is to be noted that a syn isomer of the compound (I) tends to be of much higher antimicrobial activity than the corresponding anti isomer, and accordingly the syn isomer of the compound (I) is more preferable antimicrobial agent than the corresponding anti isomer in the prophylactic and therapeutic value.

(b) The thiazolyl group of the formula:

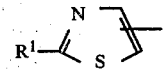

(wherein $R^1$ is as defined above) is well known to lie in tautomeric relation with a thiazolinyl group, and the tautomerism between the said thiazolyl and thiazolinyl groups can be illustrated by the following equilibrium:

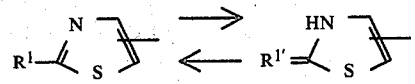

(wherein $R^1$ is as defined above, and $R^{1'}$ is imino or protected imino)

Accordingly, it is to be understood that both of the said groups are substantially the same, and the tautomers consisting of such groups are regarded as the same compounds. Therefore, both of the tautomeric forms of the compounds having such groups in their molecule are included in the scope of this invention and designated inclusively with one expression "thiazolyl" and represented by the formula:

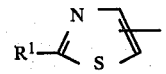

(wherein $R^1$ is as defined above) only for the convenient sake throughout this specification.

In the above and subsequent descriptions of this specification, suitable examples and illustration of the various definitions which this invention intends to include within the scope thereof are explained in detail as follows.

"Protective group" in the "protected amino" for $R^1$ may be the conventional N-protective group such as substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, acyl, or the like. Suitable acyl for the protective group may be substituted or unsubstituted lower alkanoyl (e.g. formyl, acetyl, chloroacetyl, trifluoroacetyl, etc.), substituted or unsubstituted lower alkoxycarbonyl (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, trichloroethoxycarbonyl, 2-pyridylmethoxycarbonyl, etc.), substituted or unsubstituted ar(lower)alkoxycarbonyl (e.g.

benzyloxycarbonyl, benzhydryloxycarbonyl, 4-nitrobenzyloxycarbonyl, etc.), lower cycloalkoxycarbonyl (e.g. cyclopentyloxycarbonyl, cyclohexyloxycarbonyl, etc.), 8-quinolyloxycarbonyl, succinyl, phthaloyl, or the like.

And further, the reaction product of a silan, boron, aluminium or phosphorus compound with the amino group may also be included in the protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

"Aliphatic hydrocarbon residue" for $R^2$ includes a monovalent radical of a saturated or unsaturated, and straight or branched aliphatic hydrocarbon, and particularly includes lower alkyl, lower alkenyl and lower alkynyl, the details of which are explained below.

"Lower alkyl" includes a residue of straight or branched alkane having 1 to 6 carbon atoms such as methyl, ethyl, propyl, isopropyl, butyl, isobutyl, t-butyl, pentyl, neopentyl, hexyl and the like, and preferably the one having 1 to 4 carbon atoms.

"Lower alkenyl" includes a residue of a straight or branched alkene having 2 to 6 carbon atoms, such as vinyl, allyl, 1-propenyl, isopropenyl, butenyl, isobutenyl, pentenyl, hexenyl and the like, and preferably the ones having up to 5 carbon atoms.

"Lower alkynyl" includes a residue of a straight or branched alkyne having 2 to 6 carbon atoms, such as ethynyl, propargyl, 1-propynyl, 3-butynyl, 2-butynyl, 4-pentynyl, 3-pentynyl, 2-pentynyl, 1-pentynyl, 5-hexynyl and the like, and preferably the ones having up to 5 carbon atoms.

These aliphatic hydrocarbon residue may be substituted with hydroxy, protected hydroxy or lower alkylthio. The protective group on the hydroxy group may be the same as those exemplified as the protective group on the amino group for $R^1$. "Lower alkylthio" may be methylthio, ethylthio, propylthio, isopropylthio, butylthio, isobutylthio, t-butylthio, pentylthio, hexylthio or the like.

"Heterocyclic group" for $R^3$ includes a residue of unsaturated, N- or N and S- containing, 5-membered heterocyclic compound, for example, imidazolyl, pyrazolyl, triazolyl (e.g. 1H-1,2,3-triazolyl, 4H-1,2,4-triazolyl), tetrazolyl (e.g. 1H-tetrazolyl, 2H-tetrazolyl), thiazolyl, isothiazolyl, thiadiazolyl, (e.g. 1,3,4-thiadiazolyl, 1,2,4-thiadiazolyl, 1,2,5-thiadiazolyl) and the like.

These heterocyclic groups are substituted with amino(lower)alkyl such as aminomethyl, 2-aminoethyl, 2-aminopropyl, 3-aminopropyl, 4-aminobutyl, 5-aminopentyl, 6-aminohexyl, aminoisopropyl, protected amino(lower)alkyl, or hydroxy(lower)alkyl such as hydroxymethyl, 2-hydroxyethyl, 2-hydroxypropyl, 3-hydroxypropyl, 4-hydroxybutyl, 5-hydroxypentyl, 6-hydroxyhexyl, hydroxyisopropyl. The protective group of the protected amino(lower)alkyl may be the same as those of the protected amino for $R^1$.

"Functionally modified carboxy" for $R^4$ may be an ester, amide or the like.

Suitable examples of the ester may be alkyl ester (e.g. methyl, ester, ethyl ester, propyl ester, isopropyl ester, butyl ester, isobutyl ester, t-butyl ester, pentyl ester, t-pentyl ester, hexyl ester, heptyl ester, octyl ester, 1-cyclopropylethyl ester, etc.); alkenyl ester (e.g. vinyl ester, allyl ester, etc.); alkynyl ester (e.g. ethynyl ester, propynyl ester, etc.); alkoxyalkyl ester (e.e. methoxymethyl ester, ethoxymethyl ester, isopropoxymethyl ester, 1-methoxyethyl ester, 1-ethoxyethyl ester, etc.); alkylthioalkyl ester (e.g. methylthiomethyl ester, ethylthiomethyl ester, ethylthioethyl ester, isopropylthiomethyl ester, etc); haloalkyl ester (e.g. 2-iodoethyl ester, 2,2,2-trichloroethyl ester, etc.); alkanoyloxyalkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, palmitoyloxymethyl ester, etc.); alkanesulfonylalkyl ester (e.g. mesylmethyl ester, 2-mesylethyl ester, etc.); substituted or unsubstituted aralkyl ester (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); substituted or unsubstituted aryl ester (e.g. phenyl ester, tolyl ester, t-butylphenyl ester, xylyl ester, mesityl ester, cumenyl ester, salicyl ester, etc.); an ester with a silyl compound such as trialkylsilyl compound, dialkylalkoxysilyl compound or trialkoxysilyl compound, for example, trialkylsilyl ester (e.g. trimethyl silyl ester, triethylsilyl ester, etc.), dialkylalkoxy silyl ester (e.g. dimethylmethoxysilyl ester, dimethylethoxysilyl ester, diethylmethoxysilyl ester, etc.), or trialkoxysilyl ester (e.g. trimethoxysilyl ester, triethoxysilyl ester, etc.) or the like.

With regard to the terms "protected amino" and "functionally modified carboxy", it is to be understood that these groups bear the meaning not only in synthetic manufacture of the object compound by chemical process(es), but also in physiological and pharmaceutical properties of the object compound per se.

That is, in the meaning of the synthetic manufacture, free amino group and/or free carboxy group may be transformed into the "protected amino" and/or "functionally modified carboxy" as mentioned above before conducting the process(es) for preventing any possible undesired side reaction(s), and the "protected amino" and/or "functionally modified carboxy" group in the resultant compound may be transformed into free amino and/or carboxy group after the reaction is conducted. This will be apparent from the explanation of the processes in the following.

On the other hand, in the meaning of the physiological and pharmaceutical properties of the object compound, the compound bearing the "protected amino" and/or "functionally modified carboxy" group is optionally used for improving the properties such as solubility, stability, absorbability, toxicity of the particularly active object compound bearing the free amino and/or carboxy group.

Suitable "pharmaceutically acceptable salt" of the compound (I) includes a conventional non-toxic salt, and may be a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like.

It is well known in the pharmaceutical field that the active drug, when it has any undesired physiological or pharmaceutical property such as solubility, stability, absorbability, etc., is converted into modified derivative thereof for improving such undesired properties, and then said derivative, upon administration to a patient, exhibits the active efficacy by being converted in the body to the parent drug. In this meaning, the term "pharmaceutically acceptable bioprecursor" used throughout this specification is intended to fundamentally mean all of the modified derivatives, which have structural formulae different from those of the active compounds of this invention, but are converted in the body to the active compounds of this invention upon administration, and also to mean the derivatives which are sometimes derived physiologically from the compounds of this invention in the body and exhibit antimicrobial efficacy.

The compound (I) of this invention can be prepared by processes as shown in the following scheme.

Process A : N-Acylation

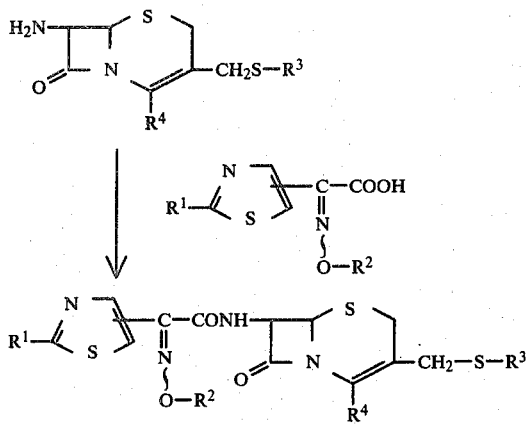

Process B : Thioetherification

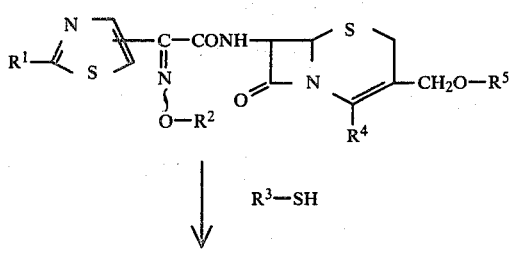

Process C : Elimination of amino-protective group in $R_a{}^1$

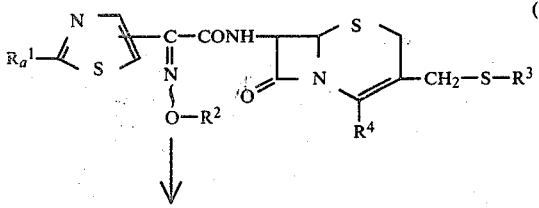

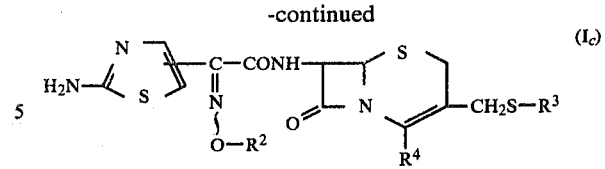

Process D : Elimination of amino-protective group in $R_a{}^3$

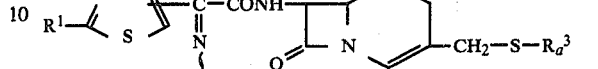

Process E : Elimination of hydroxy-protective group

wherein
$R^1$, $R^2$, $R^3$ and $R^4$ are each as defined above,
$R_a{}^1$ is protected amino,
$R_a{}^2$ is an aliphatic hydrocarbon residue substituted with protected hydroxy,
$R_b{}^2$ is an aliphatic hydrocarbon residue substituted with hydroxy,
$R_a{}^3$ is a heterocyclic group substituted with protected amino(lower)alkyl,
$R_b{}^3$ is a heterocyclic group substituted with amino(lower)alkyl, and
$R^5$ is acyl, The above processes will be explained in detail in the following.

PROCESS A

N-Acylation

A compound (I) and its salt can be prepared by reacting a 7-amino-3-cephem compound (II), its reactive derivative at the amino or a salt thereof with a carboxylic acid (III), its reactive derivative at the carboxy or a salt thereof according to a conventional manner of so-called amidation reaction well known in β-lactam chemistry.

The starting compound (III) includes both of known and new ones, and the new compound (III) can be prepared according to the methods as explained hereinafter in this specification.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with a ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorous chloride, etc.), or with a sulfur compound (e.g. thionyl choride, etc.), and the like.

Suitable salt of the compound (II) may be referred to those as exemplified for the compound (I).

Suitable reactive derivative at the carboxy group of the compound (III) may include, for example, an acid halide, an acid anhydride, an activated amide, an activated ester, and the like, and preferably acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

Suitable salt of the compound (III) may include a salt with an inorganic base such as alkali metal salt (e.g. sodium salt, potassium salt, etc.), and an alkaline earth metal salt (e.g. calcium salt, magnesium salt, etc.), a salt with an organic base such as tertiary amine (e.g. trimethylamine salt, triethylamine salt, N,N-dimethylaniline salt, pyridine salt, etc.), a salt with an inorganic acid (e.g. hydrochloride, hydrobromide, etc.) and the like.

The suitable reactive derivatives of the compounds (II) and (III) can optionally be selected from the above according to the kind of the compounds (II) and (III) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence to the reaction, or an optional mixture thereof.

When the acylating agent (III) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphoryl chloride, phosgene or the like.

In order to obtain a syn isomer of the compound (I) selectively and in high yield, it is preferable to use a syn isomer of the acylating agent (III), and to conduct the reaction under a selected reaction condition. That is, a syn isomer of the compound (I) can be obtained selectively and in high yield by conducting the reaction of a compound (II) with a syn isomer of the acylating agent (III), for example, in the presence of a Vilsmeier reagent as mentioned above and under around neutral condition.

The object compound (I) and salt thereof are useful as an antimicrobial agent, and a part thereof can also be used as a starting material in the other processes as explained below.

PROCESS B

Thioetherification

A compound (I) and its salt can be prepared by reacting a compound (IV) or its salt with a thiol compound (V) or its salt.

"Acyl" group for $R^5$ of the starting compound (IV) may be lower alkanoyl (e.g. acetyl, propionyl, etc.), aroyl (e.g. benzoyl, toluoyl, etc.) or the like.

Suitable salt of the compound (IV) may be referred to those as exemplified for the compound (I).

Suitable salt of the thiol compound (V) may be a metal salt such as alkali metal salt (e.g. sodium salt, potassium salt, etc.), and acid salt such as hydrohalide (e.g. hydrochloride, hydrobromide, etc.) or the like.

This reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, buffer solution or any other solvent which does not adversely affect the reaction, preferably in ones having strong polarities. Among the solvents, hydrophilic solvents may be used in a mixture with water. The reaction is preferably conducted in weakly basic or around neutral condition. When the compound (IV) and/or the thiol compound (V) is used in a free form, the reaction is preferably conducted in the presence of a base, for example, inorganic base such as alkali metal hydroxide, alkali metal carbonate, alkali metal bicarbonate, organic base such as trialkylamine, pyridine, and the like. The reaction temperature is not critical, and the reaction is usually carried out at ambient temperature or under warming.

PROCESS C

Elimination of amino-protective group in $R_a^1$

A compound ($I_c$) and its salt can be prepared by subjecting a compound ($I_{c'}$) or its salt to elimination reaction of the protective group in the protected amino group for $R_a^1$.

The elimination reaction may be conducted in accordance with a conventional method such as hydrolysis, reduction or the like. These methods may be selected according to the kind of the protective group to be eliminated.

The hydrolysis may include a method using an acid (acidic hydrolysis), a base (basic hydrolysis) or hydrazine, and the like. Among these methods, acidic hydrolysis is one of the common and preferable methods for eliminating the protective group such as an acyl group, for example, substituted or unsubstituted lower alkanoyl, substituted or unsubstituted lower alkoxycarbonyl, substituted or unsubstituted ar(lower)alkoxycarbonyl, lower cycloalkoxycarbonyl, substituted phenylthio, substituted alkylidene, substituted aralkylidene, substituted cycloalkylidene or the like. Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the protective group to be eliminated. The acidic hydrolysis can be conducted in the presence or absence of a solvent. Suitable solvent may be a conventional organic solvent, water or a mixture thereof, which does not adversely influence this reaction. The hydrolysis using trifluoroacetic acid is accelerated by addition of anisole.

The basic hydrolysis can be applied for eliminating the protective group such as an acyl group, preferably, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]-octane, 1,5-diazabicyclo[5,4,0]-7-undecene, anion-exchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl, for example, halo(lower)alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, etc.), 2-pyridylmethoxycarbonyl, etc.), aralkyl (e.g. benzyl, benzhydryl, trityl, etc.) and the like. Suitable reduction may include, for example, reduction using an alkali metal borohydride (e.g. sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

The reaction temperature is not critical and may be optionally selected in consideration of the chemical property of the starting compound and reaction product as well as the kind of the N-protective group and the method to be applied, and the reaction is preferably carried out under a mild condition such as under cooling, at ambient temperature or slightly elevated temperature.

The process includes in its scope the cases that the amino-protective group of the protected amino(lower)alkyl moiety in $R^3$ is eliminated and/or that the functionally modified carboxy for $R^4$ is simultaneously transformed into the free carboxy group in the course of the above reaction or in the post-treatment.

As to this process, it is to be understood that the purpose of this process lies in providing the generally more active compound ($I_c$) by eliminating the protective group in the protected amino group of the compound ($I_{c'}$) prepared by the other processes as mentioned above or below.

PROCESS D

Elimination of amino-protective group in $R_a^3$

A compound ($I_d$) and its salt can be prepared by subjecting a compound ($I_{d'}$) or its salt to elimination reaction of the protective group in the protected amino(lower)alkyl-substituted heterocyclic group for $R_a^3$.

The elimination reaction can be conducted in the same manner as the above Process C.

This process includes in its scope the cases that the amino-protective group of the protected amino for $R^1$ is eliminated and/or that the functionally modified carboxy for $R^4$ is simultaneously transformed into the free carboxy group in the course of the above reaction or the post-treatment.

PROCESS E

Elimination of hydroxy-protective group

A compound ($I_e$) and its salt can be prepared by subjecting a compound ($I_{e'}$) or its salt to elimination reaction of the protective group of the protected hydroxy group which is a substituent on the aliphatic hydrocarbon residue for $R_a^2$.

This reaction may be conducted in a similar manner to that of the aforementioned Process C.

This process includes in its scope the cases that the amino-protective group of the protected amino for $R^1$ and/or the protected amino(lower)alkyl-substituted heterocyclic group for $R^3$ is eliminated in the course of the reaction or post-treatment.

The compound obtained in accordance with the processes as explained above can be isolated and purified in a conventional manner.

In case that the object compound (I) has free amino for $R^1$, free amino(lower)alkyl-substituted heterocyclic group for $R^3$ and/or free carboxy for $R^4$, it may be transformed into its pharmaceutically acceptable salt by a conventional method.

The object compound (I), its pharmaceutically acceptable salt and bioprecursor thereof exhibit high antimicrobial activities inhibiting the growth of a wide variety of pathogenic microorganisms including Gram-positive and Gram-negative bacteria and are useful as antimicrobial agents.

In order to show the utility of the active compound (I), the test data of some representative compounds (I) are shown in the following.

1. In vitro antibacterial activity (1) Test method

In vitro antibacterial activity was determined by the two-fold agar-plate dilution method as described below.

One loopful of the 100-fold dilution of an overnight culture of each test strain in Trypticasesoy broth was streaked on heart infusion agar (HI-agar) containing graded concentrations of the test compound and incubated at 37° C. for 20 hours. The minimal inhibitory concentration (MIC) was expressed in μg/ml.

(2) Test compound

No. 1: 7-[2-(2-Aminothiazol-4-yl)-2-methoxyiminoacetamido]-3-[1-(2-hydroxyethyl)-1H-tetrazol-5-ylthiomethyl]-3-cephem-4-carboxylic acid (syn isomer)

No. 2: 7-[2-(2-Aminothiazol-4-yl)-2-methoxyiminoacetamido]-3-[1-(2-hydroxyethyl)-1H-tetrazol-5-ylthiomethyl]-3-cephem-4-carboxylic acid hydrochloride (syn isomer)

No. 3: 7-[2-(2-Aminothiazol-4-yl)-2-(2-hydroxyethoxyimino)acetamido]-3-[1-(2-hydroxyethyl)-1H-tetrazol-5-ylthiomethyl]-3-cephem-4-carboxylic acid hydrochloride (syn isomer)

No. 4: 7-[2-(2-aminothiazol-4-yl)-2-methoxyiminoacetamido]-3-(5-aminomethyl-1,3,4-thiadiazol-2-ylthiomethyl)-3-cephem-4-carboxylic acid dihydrochloride (syn isomer)

(3) Test results

MIC (μg/ml.)

| Compound No. Test strains | 1 | 2 | 3 | 4 |
|---|---|---|---|---|
| Escherichia coli NIHJ JC-2 | 0.05 | 0.39 | 0.10 | 0.05 |
| Proteus vulgaris IAM-1025 | 0.025 | 0.025 | 0.025 | 0.20 |
| Klebsiella pneumoniae 20 | 0.05 | 0.05 | 0.05 | 0.025 |
| Proteus mirabilis 18 | 0.10 | 0.20 | 0.10 | 0.10 |
| Serratia marcescens 35 | 0.78 | 1.56 | 3.13 | 3.13 |
| Enterobacter aerogenes 20 | 0.78 | 0.78 | 3.13 | 0.78 |

For prophylactic and/or therapeutic administration, the compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age and conditions of the patient, a kind of disease and a degree of the infection, and further a kind of the active compound (I) to be applied, etc., an average single dose of about 50 mg., 100 mg., 250 mg. and 500 mg. of the active compound (I) is sufficient for treating infectious diseases caused by pathogenic bacteria. In general, the active compound (I) can be administered in an amount between 1 mg/kg and 100 mg/kg, preferably 5 mg/kg and 50 mg/kg.

The starting compound (III) can be prepared as illustrated in the following, and particulars of which are to be referred to the methods described in the following Preparation.

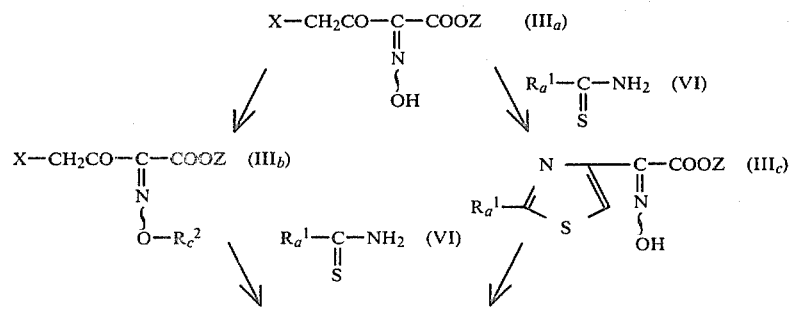

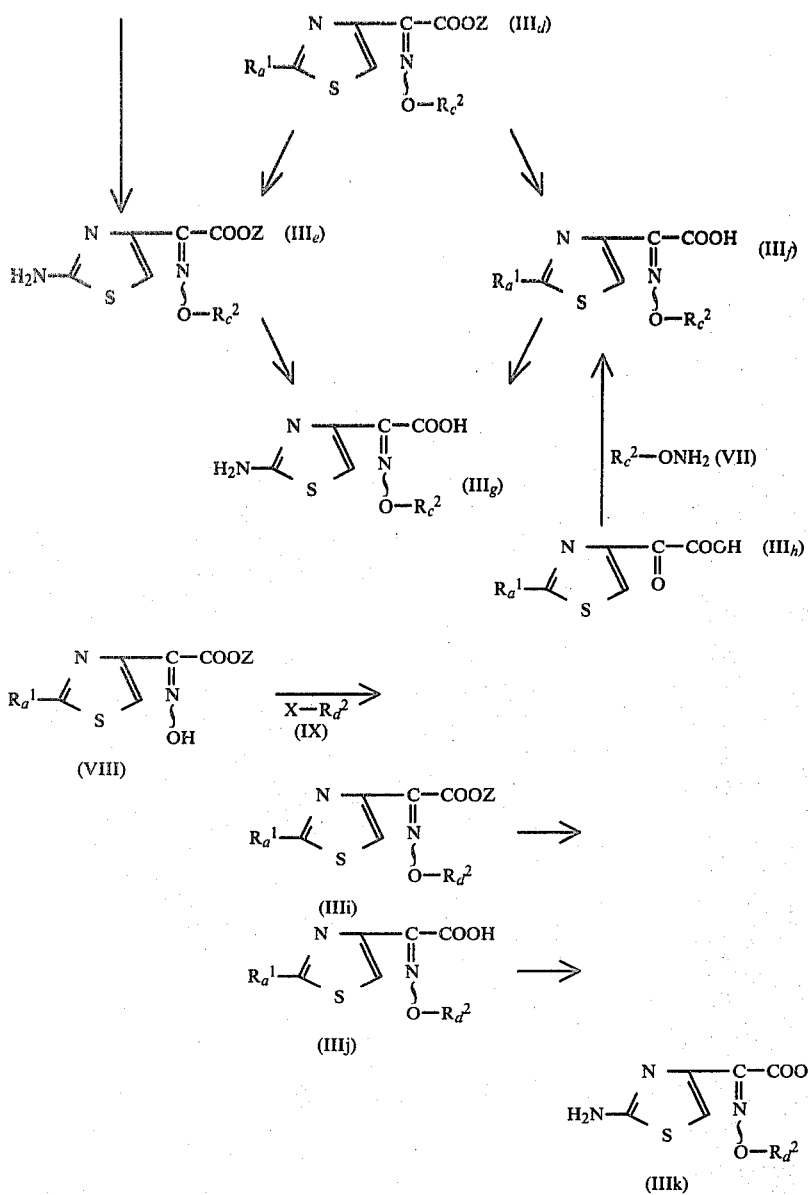

wherein
$R_a^1$ is as defined above,
$R_c^2$ is an aliphatic hydrocarbon residue which may be substituted with hydroxy or protected hydroxy,
$R_d^2$ is an aliphatic hydrocarbon residue substituted with lower alkylthio,
X is halogen, and
Z is lower alkyl

Preparation 1

(1) Allyl bromide (2.91 g) was added dropwise to a stirred suspension of ethyl 2-(2-tritylaminothiazol-4-yl)-2-hydroxyiminoacetate (syn isomer, 10 g), N,N-dimethylformamide (100 ml) and potassium carbonate (4.54 g) under ice cooling over 5 minutes, and stirred at the same temperature for 4 hours. After adding water (200 ml) to the resultant solution, the solution was extracted with diethyl ether twice. The extract was washed with a saturated aqueous solution of sodium chloride and dried over magnesium sulfate. The solution was concentrated in vacuo, and the residue was triturated with a solution of n-hexane and diethyl ether. The precipitates were collected by filtration to give ethyl 2-(2-tritylaminothiazol-4-yl)-2-allyloxyiminoacetate (syn isomer, 9.4 g), mp. 130° to 132° C.

I.R. $\nu_{max}^{Nujol}$: 3380, 1735, 1520, 1550 cm$^{-1}$.

N.M.R. δ(DMSO-d$_6$, ppm): 1.08 (3H, t, J=7 Hz), 3.96 (2H, q, J=7 Hz), 4.54 (2H, broad d, J=5 Hz), 5.0–5.5 (2H, m), 5.6–6.3 (1H, m), 6.90 (15H, broad s), 7.74 (1H, s).

(2) A solution of ethyl 2-(2-tritylaminothiazol-4-yl)-2-allyloxyiminoacetate (syn isomer, 8.7 g), 50% formic acid (42.5 ml) and tetrahydrofuran (42.5 ml) was stirred at 60° C. for 40 minutes. After concentrating the resultant solution in vacuo, the residue was dissolved in ethyl acetate, washed with an aqueous solution of sodium bicarbonate and a saturated aqueous solution of sodium chloride in turn, and dried over magnesium sulfate. After concentrating the resultant solution in vacuo, the residue was subjected to column chromatography on silica gel with benzene and ethyl acetate in turn, to give ethyl 2-(2-aminothiazol-4-yl)-2-allyloxyiminoacetate (syn isomer, 3.7 g), mp. 102° to 104° C.

I.R. $\nu_{max}^{Nujol}$: 3460, 3260, 3130, 1725, 1620, 1540, 1460 cm$^{-1}$.

N.M.R. δ(DMSO-d$_6$, ppm): 1.25 (3H, t, J=7 Hz), 4.30 (2H, q, J=7 Hz), 4.61 (2H, d,d, J=5 Hz, 1 Hz), 5.0–5.5 (2H, m), 5.6–6.5 (1H, m), 6.95 (1H, s), 7.28 (2H, s).

(3) A solution of ethyl 2-(2-aminothiazol-4-yl)-2-allyloxyiminoacetate (syn isomer, 3.6 g), 2 N aqueous solution of sodium hydroxide (14.1 ml), tetrahydrofuran (14.1 ml) and methanol (15 ml) as stirred at 40° C. for 1.5 hours. The resultant solution was concentrated in vacuo, and the residue was dissolved in water. After the solution was adjusted to pH 2.8 with 10% hydrochloric acid under ice cooling, the precipitates were collected by filtration, washed with water and acetone in turn and dried to give 2-(2-aminothiazol-4-yl)-2-allyloxyiminoacetic acid (syn isomer, 1.91 g), mp. 187° C. (dec.).

I.R. $\nu_{max}^{Nujol}$: 3350, 1630, 1580, 1460 cm$^{-1}$.

N.M.R. δ(DMSO-d$_6$, ppm): 4.61 (2H, d, J=6 Hz), 5.1–5.5 (2H, m), 5.7–6.2 (1H, m), 6.84 (1H, s), 7.25 (2H, broad s).

Preparation 2

(1) A mixture of ethyl 2-hydroxyimino-3-oxobutyrate (syn isomer, 56.7 g), N,N-dimethylformamide (280 ml), potassium carbonate (72.3 g) and propargyl bromide (43 g) was stirred at room temperature for 4 hrs. The reaction mixture was treated in a conventional manner to give ethyl 2-propargyloxyimino-3-oxobutyrate (syn isomer, 71.2 g).

I.R. $\nu_{max}^{Film}$: 3280, 3220, 2120, 1735, 1670 cm$^{-1}$.

(2) A mixture of ethyl 2-propargyloxyimino-3-oxobutyrate (syn isomer, 71.2 g), acetic acid (81 ml) and sulfuryl chloride (50.2 g) was stirred at 40° C. for 10 minutes and then at room temperature for 5.5 hrs. The reaction mixture was treated in a conventional manner to give ethyl 4-chloro-3-oxo-2-propargyloxyiminobutyrate (syn isomer, 61.6 g.), oil.

I.R. $\nu_{max}^{Film}$: 3300, 2130, 1745, 1720, 1675 cm$^{-1}$.

N.M.R. δ(CCl$_4$, ppm): 1.39 (3H, t, J=7 Hz), 2.57 (1H, t, J=2 Hz), 4.36 (2H, q, J=7 Hz), 4.56 (2H, s), 4.86 (2H, d, J=2 Hz).

(3) A mixture of ethyl 4-chloro-3-oxo-2-propargyloxyiminobutyrate (syn isomer, 61 g), thiourea (20 g), sodium acetate 3-hydrate (35.8 g), water (150 ml), and ethanol (180 ml) was stirred at 40° C. for 1.25 hrs. The reaction mixture was treated in a conventional manner to give ethyl 2-(2-aminothiazol-4-yl)-2-propargyloxyiminoacetate (syn isomer, 35.6 g).

I.R. $\nu_{max}^{Nujol}$: 3290, 2220, 1729 cm$^{-1}$.

N.M.R. δ (DMSO-d$_6$), ppm): 1.28 (3H, t, J=7 Hz), 3.49 (1H, t, J=3 Hz), 4.31 (2H, q, J=7 Hz), 4.76 (2H, d, J=3 Hz), 6.95 (1H, s), 7.29 (2H, s).

(4) A mixture of ethyl 2-(2-aminothiazol-4-yl)-2-propargyloxyiminoacetate (syn isomer, 2.8 g.), methanol (23 ml.), tetrahydrofuran (20 ml.) and 1 N aqueous solution of sodium hydroxide (22.17 ml.) was stirred at 30° C. for 5 hrs. The reaction mixture was treated in a conventional manner to give 2-(2-aminothiazol-4-yl)-2-propargyloxyiminoacetic acid (syn isomer, 1.924 g.).

I.R. $\nu_{max}^{Nujol}$: 2190, 1740 cm$^{-1}$.

N.M.R. δ (DMSO-d$_6$, ppm): 3.47 (1H, t, J=1.5 Hz), 4.74 (2H, d, J=1.5 Hz), 6.90 (1H, s).

Preparation 3

(1) A mixture of ethyl 2-hydroxyimino-3-oxobutyrate (syn isomer, 15.7 g.), 2-bromoethyl benzoate (27.5 g.), potassium carbonate (20.7 g.), N,N-dimethylformamide (25 ml.) and ethyl acetate (25 ml.) was stirred at room temperature for 4 hrs. The reaction mixture was treated in a conventional manner to give ethyl 2-(2-benzoyloxyethoxyimino)-3-oxobutyrate (syn isomer, 28 g.).

(2) A solution of 2-(2-benzoyloxyethoxyimino)-3-oxobutyrate (syn isomer, 28 g.), sulfuryl chloride (13.5 g.) and acetic acid (30 ml.) was stirred at 40° C. for 10 minutes and at room temperature for 5.5 hrs. The reaction mixture was treated in a conventional manner to give ethyl 2-(2-benzoyloxyethoxyimino)-4-chloro-3-oxobutyrate (syn isomer, 29 g.).

(3) A mixture of ethyl 2-(2-benzoyloxyethoxyimino)-4-chloro-3-oxobutyrate (syn isomer, 29 g.), thiourea (7.76 g.), sodium acetate (8.37 g.), water (75 ml.) and ethanol was stirred at 40° C. for an hour. The reaction mixture was treated in a conventional manner to give ethyl 2-(2-aminothiazol-4-yl)-2-(2-benzoyloxyethoxyimino)acetate (syn isomer, 9 g.).

N.M.R. δ (DMSO-d$_6$, ppm): 1.28 (3H, t, J=7 Hz), 4.34 (2H, q, J=7 Hz), 4.56 (4H, m), 6.44 (2H, broad s), 6.68 (1H, s), 7.68–7.34 (3H, m), 8.06 (2H, d,d, J=8 Hz, 2 Hz).

(4) A solution of ethyl 2-(2-aminothiazol-4-yl)-2-(2-benzoyloxyethoxyimino)acetate (syn isomer, 8.5 g.) in a mixture of 1 N aqueous sodium hydroxide (35 ml.), methanol (40 ml.) and tetrahydrofuran (40 ml.) was stirred at 40° C. for 9 hrs. and at room temperature for 12 hrs. The reaction mixture was treated in a conventional manner to give 2-(2-aminothiazol-4-yl)-2-(2-hydroxyethoxyimino)acetic acid (syn isomer, 3.3 g.).

I.R. $\nu_{max}^{Nujol}$: 3350, 3075, 1680, 1620 cm$^{-1}$.

N.M.R. δ (DMSO-d$_6$, ppm): 3.64 (2H, t, J=5 Hz), 4.10 (2H, t, J=5 Hz), 6.84 (1H, s), 7.16 (2H, m).

(5) A solution of formic acid (1.6 g.) and acetic anhydride (3.6 g.) was stirred at 50° C. for an hour. After cooling, 2-(2-aminothiazol-4-yl)-2-(2-hydroxyethoxyimino)acetic acid (syn isomer, 1 g.) was added to the solution and stirred at room temperature for 3 hours. Diisopropyl ether was added to the resultant solution, and the precipitates were filtered out. The filtrate was concentrated in vacuo, and the residue was pulverized with diisopropyl ether. The precipitates were collected by filtration to give 2-(2-formamidothiazol-4-yl)-2-(2-formyloxyethoxyimino)acetic acid (syn isomer, 0.7 g.).

I.R. $\nu_{max}^{Nujol}$: 3200, 1710, 1690 cm$^{-1}$.

N.M.R. δ (DMSO-d$_6$, ppm): 4.38 (4H, s), 7.58 (1H, s), 8.26 (1H, s), 8.54 (1H, s).

Preparation 4

(1) A mixture of chloromethylthiomethane (7.97 g.), powdered potassium iodide (15.1 g.) and acetone (79 ml.) was stirred at room temperature for an hour, the resulting mixture was filtered and washed with a small amount of acetone. The washings and the filtrate were combined and added to a stirred suspension of ethyl 2-(2-formamidothiazol-4-yl)-2-hydroxyiminoacetate (syn isomer, 17.5 g.) and powdered potassium carbonate (15.5 g.) in acetone (300 ml.). The mixture was stirred at room temperature for 3 hours, filtered and washed with acetone. The washings and the filtrates were combined and concentrated in vacuo. The residue was dissolved in ethyl acetate, washed with a saturated aqueous solution of sodium chloride twice, dried over magnesium sulfate and concentrated in vacuo. The oily residue was subjected to column chromatography on silica gel and eluted with chloroform to give ethyl 2-(2-formamidothiazol-4-yl)-2-methylthiomethoxyiminoacetate (syn isomer, 2.4 g.), mp. 130° to 131° C.

I.R. $\nu_{max}^{Nujol}$: 3160, 3125, 3050, 1740, 1695 cm$^{-1}$.

N.M.R. $\delta$ (DMSO-d$_6$, ppm): 1.32 (3H, t, J=7 Hz), 2.22 (3H, s), 4.38 (2H, q, J=7 Hz), 5.33 (2H, s), 7.67 (1H, s), 8.56 (1H, s).

(2) A mixture of ethyl 2-(2-formamidothiazol-4-yl)-2-methylthiomethoxyiminoacetate (syn isomer, 2.4 g.), 1 N aqueous sodium hydroxide (23.8 ml.) and methanol (19.8 ml.) was stirred at 30° C. for 2.5 hours. The resultant solution was adjusted to pH 7 with 10% hydrochloric acid and methanol was distilled off in vacuo. The aqueous solution was adjusted to pH 1 with 10% hydrochloric acid under ice cooling, and extracted with ethyl acetate three times. The extracts were washed with a saturated aqueous solution of sodium chloride, dried over magnesium sulfate and concentrated in vacuo to give 2-(2-formamidothiazol-4-yl)-2-methylthiomethoxyiminoacetic acid (syn isomer, 1.13 g.), mp. 157° C. (dec.).

I.R. $\nu_{max}^{Nujol}$: 3210, 3160, 3075, 1700, 1555 cm$^{-1}$.

N.M.R. $\delta$ (DMSO-d$_6$, ppm): 2.24 (3H, s), 5.31 (2H, s), 7.61 (1H, s), 8.57 (1H, s), 12.73 (1H, s).

EXAMPLE 1

(1) A solution of 2-(2-formamidothiazol-4-yl)-2-methoxyiminoacetic acid (syn isomer, 1.4 g) in dry ethyl acetate (20 ml) was added to a mixture of dry dimethylformamide (0.5 g), dry ethyl acetate (2.0 ml) and phosphoryl chloride (1.0 g) to give an activated acid solution. On the other hand, 7-amino-3-[1-(2-hydroxyethyl)-1H-tetrazol-5-yl-thiomethyl]-3-cephem-4-carboxylic acid (2.0 g) and trimethylsilylacetamide (5.9 g) were added to dry ethyl acetate (40 ml), stirred at 40° C. and cooled to −10° C. To the solution was added and the activated acid solution at −5° to −10° C. and stirred at the same temperature for an hour. Water (40 ml) was added to the reaction mixture and adjusted to pH 7.0 with sodium bicarbonate. The aqueous layer was separated and washed with ethyl acetate and diethyl ether successively. After removing the remaining ethyl acetate and diethyl ether by bubbling with nitrogen gas, the aqueous solution was adjusted to pH 2.0 with conc. hydrochloric acid and stirred for 30 minutes. The precipitates were collected by filtration, washed with chilled water and then dried over phosphorus pentoxide to give 7-[2-(2-formamidothiazol-4-yl)-2-methoxyiminoacetamido]-3-[1-(2-hydroxyethyl-1H-tetrazol- 5-ylthiomethyl]-3-cephem-4-carboxylic acid (syn isomer, 2.10 g).

I.R. (Nujol)$\nu$ max: 1760, 1660 cm$^{-1}$.

N.M.R. (DMSO-d$_6$) $\delta$ ppm: 3.46–4.04 (4H, m), 3.90 (3H, s), 4.12–4.53 (4H, m), 5.12 (1H, d, J=5.0 Hz), 5.79 (1H, d,d, J=5.0 Hz, 8.0 Hz), 7.42 (1H, s), 8.52 (1H, s), 9.67 (1H, d, J=8.0 Hz).

(2) A mixture of 7-[2-(2-formamidothiazol-4-yl)-2-methoxyiminoacetamido]-3-[1-(2-hydroxyethyl-1H-tetrazol-5-ylthiomethyl]-3-cephem-4-carboxylic acid (syn isomer, 2.0 g), conc.hydrochloric acid (0.73 g) and methanol (14.0 ml) was stirred at room temperature for 3 hrs. and evaporated in vacuo. The residue was dissolved in aqueous solution of sodium bicarbonate and then acidified to pH 3 with 10% hydrochloric acid. The precipitates were collected, washed with chilled water and dried over phosphorus pentoxide to give 7-[2-(2-aminothiaziol-4-yl)-2-methoxyiminoacetamido]-3-[1-(2-hydroxyethyl-1H-tetrazol-5-ylthiomethyl]-3-cephem-4-carboxylic acid (syn isomer, 1.1 g).

I.R. (Nujol) $\nu$ max: 3350, 1775, 1670, 1635 cm$^{-1}$.

N.M.R. (DMSO-d$_6$) $\delta$ ppm: 3.33–4.10 (4H, m), 3.83 (3H, s), 4.10–4.61 (4H, m), 5.11 (1H, d, J=4.3 Hz), 5.77 (1H, d,d, J=4.3 Hz, 8.0 Hz), 6.76 (1H, s), 9.60 (1H, d, J=8.0 Hz).

EXAMPLE 2

(1) A solution of 7-amino-3-[1-(2-hydroxyethyl-1H-tetrazol-5-ylthiomethyl]-3-cephem-4-carboxylic acid (2.0 g) and trimethylsilylacetamide (5.9 g) in dry ethyl acetate (40.0 ml) and a solution of 2-(2-formamidothiazol-4-yl)-2-allyloxyiminoacetic acid (syn isomer, 1.6 g), dry dimethylformamide (0.5 g) and phosphoryl chloride (1.0 g) in dry ethyl acetate 22.0 were treated in a similar manner to that of Example 1-(1) to give 7-[2-(2-formamidothiazol-4-yl)-2-allyloxyiminoacetamido]-3-[1-(2-hydroxyethyl)-1H-tetrazol-5-ylthiomethyl]-3-cephem-4-carboxylic acid (syn isomer, 2.79 g).

I.R. (Nujol) $\nu$ max: 3180, 1770, 1665 cm$^{-1}$.

N.M.R. (DMSO-d$_6$) $\delta$ ppm: 3.48–3.95 (4H, m), 4.03–4.50 (4H, m), 4.50–4.78 (2H, m), 5.01–5.54 (3H, m), 5.65–6.60 (2H, m), 7.41 (1H, s), 8.53 (1H, s), 9.67 (1H, d, J=8.5 Hz).

(2) 7-[2-(2-Formamidothiazol-4-yl)-2-allyloxyiminoacetamido]-3-[1-(2-hydroxyethyl)-1H-tetrazol-5-ylthiomethyl]-3-cephem-4-carboxylic acid (syn isomer, 2.7 g) was treated with conc.hydrochloric acid (0.94 g) in a similar manner to that of Example 1-(2) to give 7-[2-(2-aminothiazol-4-yl)-2-allyloxyiminoacetamido]-3-[1-(2-hydroxyethyl)-1H-tetrazol-5-ylthiomethyl]-3-cephem-4-carboxylic acid hydrochloride (syn isomer, 2.72 g).

I.R. (Nujol) $\nu$ max: 3340, 3210, 1772, 1730, 1665 cm$^{-1}$.

N.M.R. (DMSO-d$_6$): $\delta$ ppm: 3.44–3.83 (4H, m), 4.00–4.40 (4H, m), 4.57 (2H, m), 4.95–5.47 (3H, m), 5.53–6.74 (4H, m), 6.82 (1H, s), 9.77 (1H, d, J=8.0 Hz).

EXAMPLE 3

(1) A solution of 7-amino-3-[1-(2-hydroxyethyl)-1H-tetrazol-5-ylthiomethyl]-3-cephem-4-carboxylic acid (2.0 g) and trimethylsilylacetamide (5.9 g) in dry ethyl acetate (40.0 ml) and a solution of 2-(2-formamidothiazol-4-yl)-2-propargyloxyiminoacetic acid (syn isomer, 1.6 g), dry dimethylformamide (0.5 g) and phosphoryl chloride (1.0 g) in dry ethyl acetate (52.0 ml) were treated in a similar manner to that of Example 1-(1) to give 7-[2-(2-formamidothiazol-4-yl)-2-propargyloxyiminoacetamido]-3-[1-(2-hydroxyethyl)-1H-tetrazol-5-ylthiomethyl]-3-cephem-4-carboxylic acid (syn isomer, 2.00 g).

I.R. (Nujol) $\nu$ max: 3260, 1780, 1670 cm$^{-1}$.

N.M.R. (DMSO-d$_6$) $\delta$ ppm: 3.49 (1H, m), 3.57–4.05 (4H, m), 4.09–4.67 (4H, m), 4.79 (2H, m), 5.15 (1H, d, J=5.0 Hz), 5.81 (1H, d,d, J=5.0 Hz, 8.0 Hz), 7.46 (1H, s), 8.55 (1H, s), 9.76 (1H, d, J=8.0 Hz).

(2) 7-[2-(2-Formamidothiazol-4-yl)-2-propargyloxyiminoacetamido]-3-[1-(2-hydroxyethyl)-1H-tetrazol-5-ylthiomethyl]-3-cephem-4-carboxylic acid (syn isomer, 1.9 g) was treated with conc.hydrochloric acid (0.67 g) in a similar manner to that of Example 1-(2) to give 7-[2-(2-aminothiazol-4-yl)-2-propargyloxyiminoacetamido]-3-[1-(2-hydroxyethyl)-1H-tetrazol-5-ylthiomethyl]-3-cephem-4-carboxylic acid (syn isomer, 1.19 g).

I.R. (Nujol) $\nu$ max: 3300, 1775, 1670 cm$^{-1}$.

N.M.R. (DMSO-d$_6$) $\delta$ ppm: 3.47 (1H, m), 3.56–4.00 (4H, m), 4.00–4.56 (4H, m), 4.72 (2H, m), 5.14 (1H, d, J=5.0 Hz), 5.79 (1H, d,d, J=5.0 Hz, 8.0 Hz), 6.82 (1H, s), 9.67 (1H, d, J=8.0 Hz).

EXAMPLE 4

(1) A solution of 7-amino-3-[1-(2-hydroxyethyl)-1H-tetrazol-5-ylthiomethyl]-3-cephem-4-carboxylic acid (2.16 g) in 50% aqueous acetone (22 ml) and a solution of 2-(2-formamidothiazol-4-yl)-2-methylthiomethoxyiminoacetic acid (syn isomer, 1.5 g), dimethylformamide (0.48 g) and phosphoryl chloride (1.01 g) in tetrahydrofuran (15 ml) were treated in a similar manner to that of Example 1-(1) to give 7-[2-(2-formamidothiazol-4-yl)-2-methylthiomethoxyiminoacetamido]-3-[1-(2-hydroxyethyl)-1H-tetrazol-5-ylthiomethyl]-3-cephem-4-carboxylic acid (syn isomer, 2.58 g).

I.R. (Nujol) $\nu$ max: 3420, 3250, 3050, 1770, 1660, 1540 cm$^{-1}$.

N.M.R. (DMSO-d$_6$) $\delta$ ppm: 2.23 (3H, s), 3.52–3.97 (4H, m), 4.11–4.62 (4H, m), 5.17 (1H, d, J=5 Hz), 5.28 (2H, s), 5.85 (1H, d,d, J=5 Hz, 8 Hz), 7.47 (1H, s), 8.54 (1H, s), 9.75 (1H, d, J=8 Hz), 12.69 (1H, broad s).

(2) 7-[2-(2-Formamidothiazol-4-yl)-2-methylthiomethoxyiminoacetamido]-3-[1-(2-hydroxyethyl)-1H-tetrazol-5-ylthiomethyl]-3-cephem-4-carboxylic acid (syn isomer, 2.5 g) was treated with conc.hydrochloric acid (0.88 g) in a similar manner to that of Example 1-(2) to give 7-[2-(2-aminothiazol-4-yl)-2-methylthiomethoxyiminoacetamido]-3-[1-(2-hydroxyethyl)-1H-tetrazol-5-ylthiomethyl]-3-cephem-4-carboxylic acid (syn isomer, 1.8 g).

I.R. (Nujol) $\nu$ max: 3350, 1780, 1670, 1630, 1540 cm$^{-1}$.

N.M.R. (DMSO-d$_6$) $\delta$ ppm: 2.16 (3H, s), 3.3–3.9 (4H, m), 4.0–4.6 (4H, m), 5.08 (1H, d, J=5 Hz), 5.15 (2H, s), 5.76 (1H, d, d, J=5 Hz, 8 Hz), 6.76 (1H, s), 7.22 (2H, broad s), 9.77 (1H, d, J=8 Hz).

EXAMPLE 5

(1) A solution of 7-amino-3-[1-(2-hydroxyethyl)-1H-tetrazol-5-ylthiomethyl]-3-cephem-4-carboxylic acid (2.0 g) and trimethylsilylacetamide (5.9 g) in dry ethyl acetate (40 ml) and a solution of 2-(2-formamidothiazol-4-yl)-2-(2-formyloxyethoxyimino)acetic acid (syn isomer, 1.8 g), dry dimethylformamide (0.5 g) and phosphoryl chloride (1.0 g) in dry ethyl acetate (22.0 ml) were treated in a similar manner to that of Example 1-(1) to give 7-[2-(2-formamidothiazol-4-yl)-2-(2-formyloxyethoxyimino)acetamido]-3-[1-(2-hydroxyethyl)-1H-tetrazol-5-ylthiomethyl]-3-cephem-4-carboxylic acid (syn isomer, 1.10 g).

I.R. (Nujol) $\nu$ max: 3170, 1770, 1660 cm$^{-1}$.

N.M.R. (DMSO-d$_6$) $\delta$ ppm: 3.43–3.88 (4H, m), 3.95–4.60 (8H, m), 5.11 (1H, d, J=5.0 Hz), 5.79 (1H, d,d, J=5.0 Hz, 8.0 Hz), 7.42 (1H, s), 8.22 (1H, s), 8.51 (1H, s), 9.65 (1H, d, J=8.0 Hz).

(2) 7-[2-(2-Formamidothiazol-4-yl)-2-(2-formyloxyethoxyiminoacetamido]-3-[1-(2-hydroxyethyl)-1H-tetrazol-5-ylthiomethyl]-3-cephem-4-carboxylic acid (syn isomer, 1.0 g) was treated with conc. hydrochloric acid (0.66 g) in a similar manner to that of Example 1-(2) to give 7-[2-(2-aminothiazol-4-yl)-2-(2-hydroxyethoxyimino)acetamido]-3-[1-(2-hydroxyethyl)-1H-tetrazol-5-ylthiomethyl]-3-cephem-4-carboxylic acid (syn isomer, 0.97 g).

I.R. (KBr) $\nu$ max: 3300, 3100, 2970, 1770, 1735, 1640 cm$^{-1}$.

N.M.R. (DMSO-d$_6$) $\delta$ ppm: 3.50–3.95 (6H, m), 4.00–4.63 (6H, m), 5.14 (1H, d, J=5.0 Hz), 5.28–6.85 (3H, m), 6.93 (1H, s) 9.71 (1H, d, J=8.0 Hz).

EXAMPLE 6

(1) A solution of 7-amino-3-(5-t-butoxycarbonylaminomethyl-1,3,4-thiadiazol-2-ylthiomethyl)-3-cephem-4-carboxylic acid (4.6 g), trimethylsilylacetamide (7.86 g) and bis(trimethylsilyl)acetamide (4.0 g) in ethyl acetate (50 ml) and a solution of dimethylformamide (0.804 g), phosphoryl chloride (1.69 g) and 2-(2-formamidothiazol-4-yl)-2-methoxyiminoacetic acid (syn isomer, 12.3 g) were treated in a similar manner to that of Example 1-(1) to give 7-[2-(2-formamidothiazol-4-yl)-2-methoxyiminoacetamido]-3-(5-t-butoxycarbonylaminomethyl-1,3,4-thiadiazol-2-ylthiomethyl)-3-cephem-4-carboxylic acid (syn isomer, 4.2 g).

I.R. (Nujol) $\nu$ max: 3200–3300, 1780, 1700, 1670, 1540 cm$^{-1}$.

N.M.R. (DMSO-d$_6$) $\delta$ ppm: 1.42 (9H, s), 3.70 (2H, q, J=18 Hz), 3.92 (3H, s), 4.44 (2H, d, J=6 Hz), 4.48 (2H, q, J=14 Hz), 5.18 (1H, d, J=5 Hz), 5.84 (1H, d,d, J=5 Hz, 8 Hz), 7.44 (1H, s), 7.76 (1H, broad s), 8.52 (1H, s), 9.68 (1H, d, J=8 Hz), 12.64 (1H, broad s).

(2) Conc.hydrochloric acid (1.82 g) was added to a suspension of 7-[2-(2-formamidothiazol-4-yl)-2-methoxyiminoacetamido]-3-(5-t-butoxycarbonylaminomethyl-1,3,4-thiadiazol-2-ylthiomethyl)-3-cephem-4-carboxylic acid (syn isomer, 3.9 g) in methanol (60 ml), and the mixture was stirred at room temperature for 2 hrs. After evaporation of the solvent under reduced pressure, methanol was added to the residue and evaporated again. The residue was washed with diethyl ether and dried to give 7-[2-(2-aminothiazol-4-yl)-2-methoxyiminoacetamido]-3-(5-aminomethyl-1,3,4-thiadiazol-2-ylthiomethyl)-3-cephem-4-carboxylic acid dihydrochloride (syn isomer, 3.0 g).

I.R. (Nujol) $\nu$ max: 3200–3400, 1780, 1680, 1630, 1540 cm$^{-1}$.

N.M.R. (DMSO-d$_6$) $\delta$ ppm: 3.80 (2H, broad s), 4.03 (3H, s), 4.22 (2H, m), 4.62 (2H, m), 5.25 (1H, d, J=5 Hz), 5.85 (1H, d,d, J=5 Hz, 8 Hz), 7.05 (1H, s), 9.92 (1H, d, J=8 Hz).

EXAMPLE 7

(1) A solution of 5-aminomethyl-1,3,4-thiadiazole-2-thiol hydrochloride (2.75 g) in 0.1 M phosphate buffer (100 ml) was adjusted to pH 6.0 to 6.2 with aqueous sodium bicarbonate. To the solution was added 7-[2-(2-formamidothiazol-4-yl)-2-methoxyiminoacetamido]cephalosporanic acid (syn isomer, 4.83 g), and the mixture was stirred at 60° C. for 5 hrs. while keeping at pH 6.5 to 7.0 with aqueous sodium bicarbonate. After cooling, the reaction mixture was adjusted to pH 3 with 10% hydrochloric acid, and the precipitates were collected by filtration, washed with water and dried to give 7-[2-(2-formamidothiazol-4-yl)-2-methoxyiminoacetamido]-3-(5-aminomethyl-1,3,4-thiadiazol-2-ylthiomethyl)-3-cephem-4-carboxylic acid (syn isomer, 4,6 g).

I.R. (Nujol) ν max: 3300–3150, 1740, 1660, 1620 1540 cm$^{-1}$.

(2) Thus obtained 7-[2-(2-formamidothiazol-4-yl)-2-methoxyiminoacetamido]-3-(5-aminomethyl-1,3,4-thiadiazol-2-ylthiomethyl)-3-cephem-4-carboxylic acid (syn isomer) was treated with conc.hydrochloric acid in a similar manner to that of Example 6-(2) to give 7-[2-(2-aminothiazol-4-yl)-2-methoxyiminoacetamido]-3-(5-aminomethyl-1,3,4-thiadiazol-2-ylthiomethyl)-3-cephem-4-carboxylic acid (syn isomer).

What we claim is:

1. A syn isomer compound of the formula:

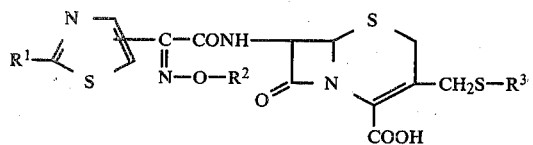

wherein
$R^1$ is amino or lower alkanoylamino,
$R^2$ is lower alkyl lower alkylthio(lower)alkyl, hydroxy(lower)alkyl, lower alkanoyloxy(lower)alkyl, lower alkenyl or lower alkynyl,
$R^3$ is tetrazolyl monosubstituted with hydroxy(lower)alkyl, and
its pharmaceutically acceptable salt.

2. A compound of claim 1,
wherein
$R^1$ is amino, and
$R^2$ is lower alkyl.

3. A compound of claim 2, which is 7-[2-(2-aminothiazol-4-yl)-2-methoxyiminoacetamido]-3-[1-(2-hydroxyethyl)-1H-tetrazol-5-ylthiomethyl]-3-cephem-4-carboxylic acid (syn isomer).

4. A compound of claim 1,
wherein
$R^1$ is amino, and
$R^2$ is lower alkylthio(lower)alkyl, hydroxy(lower)alkyl, lower alkenyl or lower alkynyl.

5. A compound of claim 4, which is 7-[2-(2-aminothiazol-4-yl)-2-methylthiomethoxyiminoacetamido]-3-[1-(2-hydroxyethyl)-1H-tetrazol-5-ylthiomethyl]-3-cephem-4-carboxylic acid (syn isomer).

6. A compound of claim 4, which is 7-[2-(2-aminothiazol-4-yl)-2-(2-hydroxyethoxyimino)-acetamido]-3-[1-(2-hydroxyethyl)-1H-tetrazol-5-ylthiomethyl]-3-cephem-4-carboxylic acid (syn isomer).

7. A compound of claim 4, which is 7-[2-(2-aminothiazol-4-yl)-2-allyloxyiminoacetamido]-3-[1-(2-hydroxyethyl)-1H-tetrazol-5-ylthiomethyl]-3-cephem-4-carboxylic acid (syn isomer).

8. A compound of claim 4, which is 7-[2-(2-aminothiazol-4-yl)-2-(propargyloxyiminoacetamido]-3-[1-(2-hydroxyethyl)-1H-tetrazol-5-ylthiomethyl]-3-cephem-4-carboxylic acid (syn isomer).

* * * * *